United States Patent
Klee

(10) Patent No.: US 8,044,113 B2
(45) Date of Patent: Oct. 25, 2011

(54) DENTAL ROOT CANAL FILLING MATERIAL

(75) Inventor: Joachim E. Klee, Radolfzell (DE)

(73) Assignee: Dentsply International, Inc, York, PA (US)

( * ) Notice: Subject to any disclaimer, the term of this patent is extended or adjusted under 35 U.S.C. 154(b) by 776 days.

(21) Appl. No.: 10/596,742

(22) PCT Filed: Dec. 17, 2004

(86) PCT No.: PCT/EP2004/014430
§ 371 (c)(1),
(2), (4) Date: Feb. 11, 2008

(87) PCT Pub. No.: WO2005/063171
PCT Pub. Date: Jul. 14, 2005

(65) Prior Publication Data
US 2008/0234404 A1    Sep. 25, 2008

(30) Foreign Application Priority Data

Dec. 23, 2003 (EP) .................................... 03029825

(51) Int. Cl.
*A61K 6/08* (2006.01)
(52) U.S. Cl. ........................................ 523/116; 523/117
(58) Field of Classification Search .................. 523/116, 523/117
See application file for complete search history.

(56) References Cited

U.S. PATENT DOCUMENTS

| 5,624,976 | A | 4/1997 | Klee |
| 2002/0143108 | A1 | 10/2002 | Klee et al. |
| 2003/0045604 | A1 | 3/2003 | Klee |

FOREIGN PATENT DOCUMENTS

| EP | 0 673 637 A1 | 9/1995 |
| EP | 1 548 021 A1 | 6/2005 |
| WO | 02/13767 A2 | 2/2002 |
| WO | 02/13768 A2 | 2/2002 |

OTHER PUBLICATIONS

M. Venturi, C Prati, G. Capelli, M. Falconi, L. Breschi, A Preliminary Analysis of the Morphology of Lateral Canals After Root Canal Filing Using a Tooth-Clearing Technique, Int. Endod. J., 2003, pp. 54-63, vol. 36.
I. Miletić, I. Anić, S. Pezelj-Ribarć, S. Jukić, Leakage of Five Root Canal Sealers, Int. Endod. J., 1999, pp. 415-418, vol. 32.
J.E. Siqueira, Jr., I. N. Rocas, C.R.A. Valois, Apical Sealing Ability of Five Endodontic Sealers, Aust. Endod. J., 2001, pp. 33-35.
Y. Haikel, W. Wittenmeyer, G. Bateman, A. Bentaleb, C. Allemann, A New Method for the Quantitative Analysis of Endodontic Microleakage, J. Endod., 1999, pp. 172-177, vol. 25, No. 3.
E.A. Koulaouzidou, K. T. Papazisis, P. Beltes, G.D. Geromichalos, A. H. Kortsaris, Cytotoxicity of Three Resin-Based Root Canal Sealers: an in vitro Evaluation, Endod. Dent. Traumatol., 1998, pp. 182-185, vol. 14.
I. Miletić, I. Anić, Z. Karlović, T. Marsan, S. Pezelj-Ribarić, M. Osmak, Cytotoxic Effect of Four Root Filing Materials, Endod. Dent. Traumatol, 2000, pp. 287-290, vol. 16.
B. Cohen, M. Pagnillo, B.L. Musikant, A. Deutsch, An In Vitro Study of the Cytotoxicity of Two Root Canal Sealers, J. Endod., 2000, pp. 228-229, vol. 26, No. 4.
N.G. Azar, M. Heidari, Z.S. Bahrami, F. Sitokri, In Vitro Cytotoxicity of a New Epoxy Resin Root Canal Sealer, J. Endod., 2000, pp. 462-465, vol. 26, No. 8.

*Primary Examiner* — Edward J Cain
(74) *Attorney, Agent, or Firm* — Douglas J. Hura; David A. Zdurne; Leana Levin

(57) ABSTRACT

A dental root canal sealing composition curable in the absence of a polymerisation initiator, which comprises (i) an amino terminated prepolymer having a viscosity at 23° C. of less than 100 Pas. (ii) a compound capable of undergoing polyaddition with the aminoterminated prepolymer (i); (iii) 40 to 85 wt.-% of a filler for providing a minimum radioopacity of at least 3 mm/mm Al.

12 Claims, No Drawings

DENTAL ROOT CANAL FILLING MATERIAL

FIELD OF THE INVENTION

The present invention relates to a dental root canal sealing composition curable by addition polymerisation in the absence of a polymerisation catalyst.

BACKGROUND OF THE INVENTION

Dental root canal sealing compositions are frequently applied into the root canal through a canal of a needle. Due to the small dimensions of the needle canal, the compositions are required to have a low viscosity. Alternatively, dental root canal sealing compositions are applied by using lentulos or gutta percha tips. Accordingly, the viscosity must be low so that thin films may be formed. Independent from the application technique, the viscosity of the material must be low enough so that the composition may enter into dentin canals in the root canal.

The application of dental root canal sealing compositions is checked by using X-ray procedures. Due to the requirement for radioopacity, the compositions are required to contain a substantial amount of a radioopaque filler.

Dental root canal sealing compositions are known from WO 02/13767 disclosing in the application examples a two-component paste/paste system. The two-component paste/paste system is based on addition polymerisation of equimolar amounts of low-molecular diamines and low-molecular diacrylates optionally in the presence of a reactive diluent for ajusting the viscosity of the composition.

Recently, root canal sealing materials composed of primary monoamines and/or disecondary diamines and diepoxides (U.S. Pat. No. 5,624,976), diacrylates (WO 02/13767) and bisacrylamides (WO 02/13768) were disclosed. These materials exhibit some advantageous properties such as relative long working time due to the slow addition polymerisation, high radio opacity, low volumetric shrinkage, low solubility and a tight sealing ability (Int. Endod. J. January 2003; 36 (1):54-63; Int. Endod. J. September 1999; 32 (5): 415-8; Aust. Endod. J. April 2001; 27 (1): 33-5; J. Endod. March 1999; 25 (3): 172-7)).

However, the presence of low molecular amines in the dental root canal sealing composition leads to severe drawbacks. Cytotoxic effects are frequently observed due to leaching of such amines from the root canal. Moreover, the cured compositions of WO 02/13767 show a considerable solubility whereby the cytotoxicity problem is aggravated and further application problems are created. Finally, the high vapor pressure of low molecular amines and the high penetration rate through plastic packaging render the compositions of WO 02/13767 problematic for industrial application. (Endod. Dent. Traumatol. August 1998; 14 (4): 182-5; Endod. Dent. Traumatol. December 2000; 16 (6): 287-90; J. Endod. August 2000; 26 (8): 462-5; J. Endod. April 2000; 26 (4): 228-9)).

Polyaminoesters specifically disclosed in WO 02/13767 are highly viscous and require the use of a substantial amount of reactive diluent in order to decrease the viscosity. However, reactive diluents cannot be polymerised by addition polymerisation, but require the presence of a polymerisation initiator.

US2002/0143108 discloses polymeriable macromonomers obtainable by a two-step reaction wherein in a first step a diepoxide is reacted with a disecondary diamine for providing an intermediate prepolymer which is reacted in a second step with 2,3-epoxypropyl-(meth)acrylate. According to the corresponding Referential Example 5, the intermediate prepolymer is not isolated. Accordingly, US2002/0143108 cannot disclose the intermediate prepolymer. Moreover, US2002/0143108 does not disclose an intermediate prepolymer suitable for providing an amino terminated prepolymer having a viscosity at 23° C. of less than 100 Pas.

It is the problem of the present invention to provide a dental root canal sealing composition having a low viscosity, low cytotoxicity, and low solubility while having excellent mechanical properties such as low shrinkage and flexibility and which do not give rise to handling problems during manufacture and application.

SUMMARY OF THE INVENTION

This problem is solved according to the claims. The present invention provides a dental root canal sealing composition curable in the absence of a polymerisation initiator, which comprises (i) an amino terminated prepolymer having a viscosity at 23° C. of less than 100 Pas, which is obtainable by reacting
  (a) one mole of a compound of the following formula (I)

wherein
  Z represents
    an n-valent $C_{2-42}$ hydrocarbon group, which groups may contain 1 to 6 oxygen atoms, and which may be substituted by 1 to 6 $C_{1-4}$ alkyl groups;
  X represents
    a single bond or
    an oxygen atom or a nitrogen atom substituted by a $C_{1-6}$ alkyl group;
  L represents
    a single bond or
    an optionally substituted $C_{1-6}$ alkylene group,
    an optionally substituted $C_{6-14}$ arylene group,
    an optionally substituted $C_{7-16}$ alkylenearylene group,
    an optionally substituted $C_{7-16}$ arylenealkylene group,
    which groups may be substituted by 1 to 6 $C_{1-4}$ alkyl groups; and
  n represents
    an integer of from 2 to 6; and
(b) at least n moles of one or more compounds
(b1) of the following formula (II)

wherein
  A represents a divalent saturated aliphatic $C_{2-16}$ hydrocarbon group or a divalent saturated cycloaliphatic $C_{3-6}$ hydrocarbon group, which groups may contain 1 to 6 oxygen atoms, and which may be substituted by 1 to 6 $C_{1-4}$ alkyl groups;

$R_a$ and $R_b$ are the same or different and represent
a hydrogen atom, a $C_{1-6}$ alkyl or a $C_{3-4}$ cycloalkyl group, which may be substituted by one or more members of the group selected from a $C_{1-4}$ alkyl group, $C_{1-4}$ alkoxy group, a phenyl group, and a hydroxy group; or (b2) of the following formula (III)

R'NH$_2$  (III)

wherein R' represents
a substituted or unsubstituted $C_1$ to $C_{18}$ alkyl group,
a substituted or unsubstituted $C_3$ to $C_{18}$ cycloalkyl group,
a substituted or unsubstituted $C_7$ to $C_{30}$ aralkyl group, which groups may be substituted by one or more members of the group selected from a $C_{1-4}$ alkyl group, $C_{1-4}$ alkoxy group, a phenyl group, and a hydroxy group,
optionally in combination with a further di- or polyamine compound;

(ii) a compound capable of undergoing polyaddition with the aminoterminated prepolymer (i);

(iii) 40 to 85 wt.-% of a filler for providing a minimum radioopacity of at least 3 mm/mm Al.

The present invention also provides a use of the amino terminated prepolymer having a viscosity at 23° C. of less than 100 Pas in a dental composition, preferably a dental root canal sealing composition.

DESCRIPTION OF THE PREFERRED EMBODIMENTS

In the formula (I), Z is an n-valent $C_{2-42}$ hydrocarbon group optionally containing 1 to 6 oxygen atoms, and which may be substituted by 1 to 6 $C_{1-4}$ alkyl groups. Preferably, Z is an n-valent $C_{2-22}$ hydrocarbon group. Z may be divalent (n=2), trivalent (n=3), tetravalent (n=4), pentavalent (n=5), or hexavalent (n=6). Preferable Z is divalent or trivalent, most preferably divalent. The hydrocarbon group may be substituted by 1 to 6 $C_{1-4}$ alkyl groups. Specific examples of the alkyl groups are methyl, ethyl, n-propyl, i-propyl, n-butyl, i-butyl or tert.-butyl. The hydrocarbon group may contain 1 to 6 oxygen atoms in the hydrocarbon group in the form of aliphatic or aromatic ether bonds, keto groups, carboxylic acid groups, hydroxyl groups, or ester groups. Specifically, Z may be a divalent substituted or unsubstituted $C_1$ to $C_{18}$ alkylene group, substituted or unsubstituted $C_{6-14}$ arylene group, substituted or unsubstituted $C_3$ to $C_{18}$ cycloalkylene group, substituted or unsubstituted $C_7$ to $C_{30}$ arylenealkylenearylene group. Preferably, Z represents a saturated aliphatic $C_{2-18}$ hydrocarbon chain which may contain 2 to 4 oxygen atoms, and which may be substituted by 1 to 6 $C_{1-4}$ alkyl groups, or Z may be a substituted or unsubstituted $C_7$ to $C_{30}$ arylenealkylenearylene group which may be substituted by 1 to 6 $C_{1-4}$ alkyl groups. In particular, Z may be an alkylene group or a 2,2-bis(phenylene)propane group —$C_6H_4C(CH_3)_2C_6H_4$—.

In formula (I), X represents a single bond or an oxygen atom or a nitrogen atom substituted by a $C_{1-6}$ alkyl group. Preferably, X is an oxygen atom.

In formula (I), L may be a single bond or an optionally substituted $C_{1-16}$ alkylene group, an optionally substituted $C_{6-14}$ arylene group, an optionally substituted $C_{7-16}$ alkylenearylene group, an optionally substituted $C_{7-16}$ arylenealkylene group, which groups may be substituted by 1 to 6 $C_{1-4}$ alkyl groups. Examples for a $C_{1-16}$ alkylene group are methylen, ethylene, propylene or butylene. Examples for a $C_{6-14}$ arylene group are p-phenylene or m-phenylene. Examples for a $C_{7-16}$ alkylenearylene group are —(CH$_2$)$_x$C$_6$H$_5$—, wherein x is an integer of from 1 to 6. Examples for a $C_{7-16}$ arylenealkylene group are —C$_6$H$_5$(CH$_2$)$_x$—, wherein x is an integer of from 1 to 6. Preferably, L is an optionally substituted $C_{1-16}$ alkylene group, in particular a methylene group.

In a preferred embodiment, X is an oxygen atom and/or L is an alkylene group, preferably a methylene group, and/or X-L is —OCH$_2$—.

In formula (II), A is a divalent saturated aliphatic $C_{2-16}$ hydrocarbon group or a divalent saturated cycloaliphatic $C_{3-6}$ hydrocarbon group, which groups may be based on linear or branched alkylene groups having 2 to 16 carbon atoms, preferably 4 to 10 carbon atoms, or cycloalkylene groups having 3 to 6 carbon atoms, preferably 4 to 6 carbon atoms. The hydrocarbon group may be substituted by one or more $C_{1-4}$ alkyl groups. Specific examples of the alkyl groups are methyl, ethyl, n-propyl, i-propyl, n-butyl, i-butyl or tert.-butyl. The hydrocarbon group may contain 1 to 6 oxygen atoms in the carbon chain connecting the amino groups or in a side chain. Preferably the divalent saturated aliphatic $C_{2-16}$ hydrocarbon group or the divalent saturated cycloaliphatic $C_{3-6}$ hydrocarbon group is highly flexible due to the presence of ether bonds and the absence of bulky groups. In a preferred embodiment, A is a divalent group based on a straight chain alkylene group which may contain ether bonds. In a preferred embodiment, A may be —(CH$_2$)$_2$O(CH$_2$)$_2$O(CH$_2$)$_2$—.

$R_a$ and $R_b$ may the same or different and represent a hydrogen atom, a $C_{1-6}$ alkyl or a $C_{3-14}$ cycloalkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. Examples of the $C_{3-14}$ cycloalkyl group can include those having 3 to 14 carbon atoms, for example, cyclopropyl, cyclobutyl, cyclopentyl and cyclohexyl. The $C_{1-6}$ alkyl group and the $C_{3-14}$ cycloalkyl group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy. Preferably, $R_a$ and $R_b$ are hydrogen.

In the preparation of the prepolymer, the compound of formula (II) may be used in combination with an amine compound of the formula RNH$_2$, wherein R represents $C_{1-6}$ alkyl or a $C_{3-14}$ cycloalkyl group, which may be substituted by one or more members of the group selected from a $C_{1-4}$ alkyl group, $C_{1-4}$ alkoxy group, a phenyl group, and a hydroxy group, or a further di- or polyamine compound. The amine of the formula $R_a$NH$_2$ and/or the further di- or polyamine compound may be used to replace up to n/1.5 moles, preferably n/20 to n/2 moles of the compound of formula (II) used in the reaction for preparing the prepolymer, wherein n is as defined above. The amount of the component used in combination with the diamine of formula (II) must be chosen such that the viscosity of the prepolymer does not exceed 100 Pa*s, preferably 80 Pa*s, more preferably 20 Pa*s.

Preferred amino terminated prepolymers are characterized by the following formulas:

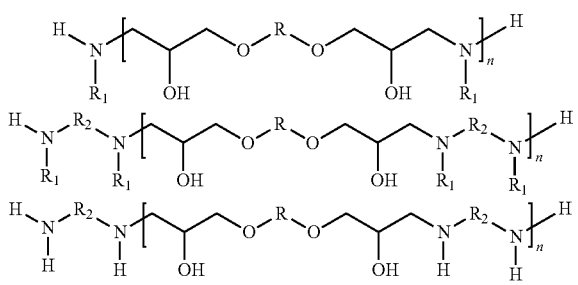

wherein
R represents Z as defined in claim 1, preferably a divalent
substituted or unsubstituted $C_1$ to $C_{18}$ alkylene group,
substituted or unsubstituted $C_{6-14}$ arylene group,
substituted or unsubstituted $C_3$ to $C_{18}$ cycloalkylene group,
substituted or unsubstituted $C_7$ to $C_{30}$ arylenealkylene-arylene group,
$R_1$ represents
hydrogen or
a substituted or unsubstituted $C_1$ to $C_{18}$ alkyl group,
a substituted or unsubstituted $C_3$ to $C_{18}$ cycloalkyl group,
a substituted or unsubstituted $C_7$ to $C_{30}$ aralkyl group,
$R_2$ represents a divalent
substituted or unsubstituted $C_1$ to $C_{18}$ alkylene group,
a substituted or unsubstituted $C_3$ to $C_{18}$ cycloalkylene group,
a substituted or unsubstituted $C_7$ to $C_{30}$ aralkylene group, and
n is an integer.

Most preferably, the aminoterminated prepolymer is a prepolymer of one of the following formulas:

wherein $R^1$ and $R^2$ are as defined above.

The application of amino terminated prepolymers as one component for a root canal filling material is advantageous because the content of low molecular amines is strongly reduced. Therefore, the compatibility with packaging materials as well as biocompatibility are improved. Furthermore, the polymerisation shrinkage is reduced.

The synthesis of secondary amine terminated epoxide-amine prepolymers was described by Klee (Acta Polym. 37(1986) 272; Angew. Makromol. Chem. 147 (1987) 71; Acta Polym. 45 (1994) 73). These prepolymers are not applied either for further addition polymerisation nor for compositions of root canal sealers.

The compound capable of undergoing polyaddition with the aminoterminated prepolymer (i) is selected from a di- or polyfunctional acrylate, a di- or polyfunctional epoxide, a di- or polyfunctional isocyanate, a di- or polyfunctional isothiocyanate, a di- or polyfunctional acylamide, or a di- or polyfunctional maleimide.

The dental root canal sealing material polymerises by addition polymerisation of amino terminated prepolymers and di- or polyfunctional epoxides, acrylates, acrylamides, maleinimides, isocyanates, thioisocyanates immediately after homogeneous mixing of the compounds.

Due to the application of radio-opaque fillers a radio-opacity of at least 3 mm/mm Al, preferably at least 5 to 7 mm/mm Al, most preferably at least 7 mm/mm Al is provided. As fillers the following compounds are suitable: inorganic fillers such as $La_2O_3$, $ZrO_2$, $BiPO_4$, $CaWO_4$, $BaWO_4$, $SrF_2$, $Bi_2O_3$, organic fillers, such as polymer granulate or a combination of organic and/or inorganic fillers.

The dental root canal sealing composition of the invention contains 40 to 85 wt.-% of a filler for providing a minimum

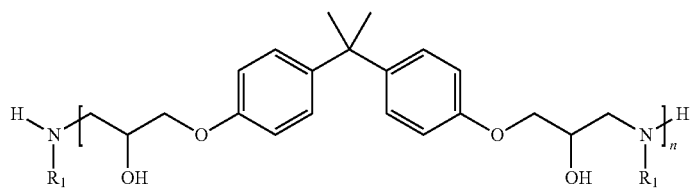

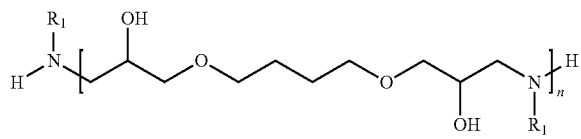

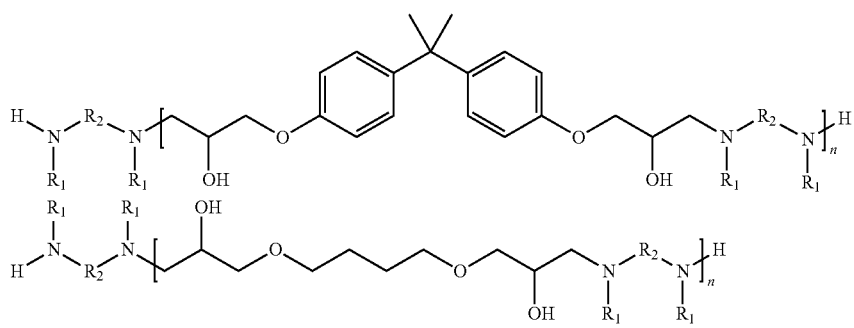

radioopacity of the cured composition of at least 3 mm/mm Al. The filler contains $La_2O_3$, $ZrO_2$, $BiPO_4$, $CaWO_4$, $BaWO_4$, $SrF_2$, $Bi_2O_3$. The radioopacity of the cured composition of the invention is at least 3 mm/mm Al, preferably at least 5 to 7 mm/mm Al, and most preferably at least 7 mm/mm Al.

The dental root canal filling material is usable to form prefabricated root canal cones of the same material as applied for the sealing in order to guarantee the compatibility between sealer and cones for a tight sealing.

Preferably, the dental root canal sealing composition of the invention does not contain a diluent, in particular a reactive diluent, having a viscosity which is lower than the viscosity of the prepolymer of the invention. Moreover, the dental root canal sealing composition does not need to contain a polymerisation initiator. In a preferred embodiment, the dental root canal sealing composition consists essentially of components (i) to (iii). A dental root canal sealing composition consisting essentially of components (i) to (iii) may contain common additives used in the dental field such as colorants, antibiotic agents and ion releasing agents, in a total amount of not more than 25 wt.-%, preferably not more than 10 wt.% of the composition.

A preferred embodiment of the dental root canal sealing composition of the invention contains 40 to 85 wt.-% of a filler and 15 to 60 wt.-% of the aminoterminated prepolymer and the compound capable of undergoing polyaddition with the aminoterminated prepolymer. The aminoterminated prepolymer used in the present invention is usually a mixture of oligomers. Accordingly, the amount of the aminoterminated prepolymer and the compound capable of undergoing polyaddition with the aminoterminated prepolymer is calculated based on the mixture of oligomers.

The dental root canal sealing composition of the present invention is preferably a two component composition which is mixed prior to use. The two component composition is preferably a powder/liquid system, a powder/paste system, a paste/paste system or a liquid/paste system. The paste/paste system or a liquid/paste system may be applied by an applicator wherein both components are mixed by a static mixer.

The present invention is based on the recognition that the addition of specific diamines to specific di- and oligoepoxide compounds provides prepolymers having low viscosity while at the same time eliminating the problems associated with the presence of low molecular amines.

The prepolymer contained in the dental root canal sealing composition of the present invention has a viscosity at 23° C. of less than 100 Pa*s. Preferably, the viscosity of the prepolymer is in the range of from 1 to 80 Pa*s, more preferably from 1 to 20 Pa*s. If the viscosity is too high, then it will be difficult to apply the composition through the canal of a needle. If the viscosity is too low, then it will be difficult handle the composition.

The dental root canal sealing composition of the present invention is curable in the absence of a polymerisation initiator. The curing mechanism is based on an addition reaction of an addition reaction between the aminoterminated prepolymer (i) and a compound capable of undergoing polyaddition with the aminoterminated prepolymer (i). The compound capable of undergoing polyaddition with the aminoterminated prepolymer (i) is preferably a member of the group of di- or polyfunctional acrylates, di- or polyfunctional epoxides, di- or polyfunctional isocyanates, di- or polyfunctional isothiocyanates, di- or polyfunctional acylamide, or di- or polyfunctional maleimide. Di- or polyfunctional acrylates and di- or polyfunctional maleimide are preferred with regard to the selectivity in the reaction with primary and secondary amino groups.

The use of the specific amino terminated prepolymers eliminates or at least strongly reduces the problems associated with low molecular amines. Moreover, it is surprising that the use of the specific prepolymers provides a dental root canal sealing composition which has a low viscosity. For this purpose, it is essential that rigid moieties in the prepolymers are avoided.

The compositions of the present invention may be applied to a root canal by using conventional techniques. Specifically, the compositions of the present invention may be applied via the canal of a syringe into the root canal. Moreover, the compositions of the present invention may also be used for the manufacture of prefabricated root canal cones. If cones made of the compositions of the invention are used in combination with the respective dental root canal sealing composition of the invention, compatibility of the cones with the sealing composition can be guaranteed whereby a tight seal may be obtained. The cured product obtained with the composition according to the invention has superior mechanical properties, in particular with regard to flexibility, which is essential for the application as a root canal sealing composition.

Now, the general process for the preparation of the an amino terminated prepolymer will be disclosed. The prepolymer is obtainable by reacting (a) one mole of a compound of the following formula (I)

wherein
  X and Z are as defined above and
  n represents an integer of from 2 to 6; and
(b) at least n moles of one or more compounds
(b1) of the following formula (II)

wherein wherein A, $R_a$, and $R_b$ are as defined above; and/or
(b2) of the following formula (III)

$R'NH_2$, wherein R' is as defined above;
optionally in combination with a further di- or polyamine compound.

The reaction may be carried out in the absence of a solvent or in the presence of a suitable solvent. The temperature of the reaction is preferably in the range of from 10° C. to 150° C., more preferably in the range of 20° C. to 80° C. The reaction time depends on the temperature and the reactivity of the reaction system and is usually in the range of from hours to several days. The termination of the reaction may be checked by conventional methods such as an IR spectrum whereby the end of the reaction is reached when all acrylic carbon-carbon double bonds have disappeared. In case the reaction is carried out in the absence of a solvent, the prepolymers obtained by the reaction of compounds (I) and (II) may be used as such without further work-up of the reaction mixture. In the preparation of the prepolymer, the compound of formula (II) may be used in combination with an amine of the formula $R_aNH_2$ wherein $R_a$ is as defined above. The amine of the formula $R_aNH_2$ may be used to replace of from n/10 to n/2 moles of the compound of formula (II) used in the reaction for preparing the prepolymer.

The present invention will now be further explained with reference to specific examples. Dynamic viscosities were measured by using a Bohlin CS50 rheometer at 23° C.

EXAMPLES

Example 1

JK 5-99-3

25.000 g (233.30 mmol) benzyl amine and 23.592 g (116.65 mmol) 1,4-butandiol diglycidyl ether were homogeneously mixed under heating and polymerised for 24 hours at 50° C.

Yield: 48.592 (100% of th.)

$\eta_{23°C.}=2.377\pm0.041$ Pa*s $C_{24}H_{36}N_2O_4$; 416.56

IR: 3028, 2863, 2860 ($CH_2/CH_3$), 1451, 1105, 738 ($CH_2/CH_3$) $cm^{-1}$ $^{13}$C-NMR: 137.2 (4), 128.3 (2), 128.1 (3), 126.8 (1), 75.2 (8), 71.5 (7), 70.5 (9), 57.8 (5), 55.5 (6), 27.3 (10) ppm

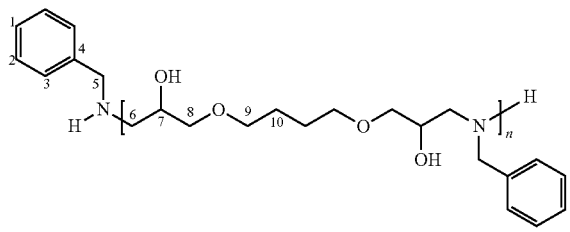

JK5-102-3: 2.784 g (6.683 mmol) of the prepared prepolymer were homogeneously mixed with 3.422 g (6.683 mmol) ethoxylated bisphenol A diacrylate (SR-601, Sartomer) and reacted at 37° C.

Example 2

JK 5-109-1

29.357 g (198.08 mmol) 2,2-(Ethylendioxy)-diethylene amine and 20.031 g (99.04 mmol) 1,4-butandiol diglycidyl ether were homogeneously mixed and polymerised for 7 days at 60° C.

Yield: 49.388 (100% of th.)

$\eta_{23°C.}=12.900\pm0.420$ Pa*s $C_{22}H_{50}N_4O_8$; 498.66.

IR: 3497 (OH), 2924; 2866 ($CH_2/CH_3$), 1454, 1340 ($CH_2/CH_3$); 1252 (C—O—C); 1099 (CH—OH) $cm^{-1}$

JK 5-109-3: 2.000 g (4.011 mmol) of the prepared prepolymer were homogeneously mixed with 2.053 g (4.011 mmol) ethoxylated bisphenol A diacrylate (SR-601, Sartomer) and reacted at 37° C. Formation of a gel occurs at 37° C. after 30 minutes.

JK 5-109-4: 2.000 g (4.011 mmol) of the prepared prepolymer were homogeneously mixed with 1.317 g (4.011 mmol) 3,(4),8,(9)-bis(acrylamido methyl) tricyclo-5.2.1.0$^{2,6}$ decane and reacted at 37° C. Formation of a gel occurs at 37° C. after 14 hours.

Example 3

10.000 g (29.375 mmol) bis-2,2-[4-(2,3-epoxypropoxy)-phenyl]-propane and 6.296 g (58.751 mmol) benzyl amine were homogeneously mixed under heating and polymerised for 20 hours at 100° C.

Yield: 16.296 (100% of th.)

$C_{35}H_{42}N_2O_4$; 554.73$M_n$(vpo) 620 g/mol, $T_g$ 11° C.

Example 4

10.000 g (29.375 mmol) bis-2,2-[4-(2,3-epoxypropoxy)-phenyl]-propane and 4.722 g (44.063 mmol) benzyl amine were homogeneously mixed under heating and polymerised for 20 hours at 100° C.

Yield: 14.722 (100% of th.)

$C_{63}H_{75}N_3O_8$; 1002.30 g/mol$M_n$(vpo) 1100 g/mol, $T_g$ 30° C.

Application Example 1

Prepolymer-Paste 4.870 g (9.77 mmol) of amino terminated prepolymer prepared by addition reaction of 2,2-(Ethylendioxy)-diethylene amine and 1,4-butane diol diglycidyl ether according example 2, 9.325 g calcium tungstate, 2.331 g zirconium oxide and 0.541 g Aerosil A 200 were homogeneously mixed.

Diacrylate-Paste 5.000 g (9.77 mmol) ethoxylated bisphenol A diacrylate (SR-601, Sartomer). 9.917 g calcium tungstate, 2.479 g zirconium oxide, 0.050 g arosil A 200 and 0.025 g iron (III) oxide were homogeneously mixed.

Immediately prior use 0.977 g Prepolymer-Paste and 1.000 g Diacrylate-Paste were mixed homogeneously and polymerised at 37° C. for 1 hour. The radio-opacity according ISO 6876 is 11.9 mm/mm Al.

Application Example 2

Prepolymer-Paste 1.871 g (3.75 mmol) of amino terminated prepolymer prepared by addition reaction of 2,2-(Ethylendioxy)-diethylene amine and 1,4-butane diol diglycidyl ether according example 2, 4.461 g calcium tungstate, 1.115 g zirconium oxide and 0.208 g Aerosil A 200 were homogeneously mixed.

Diacrylamide-Paste 1.000 g (4.20 mmol) N,N'-Bisacrylamido-N,N'-diethyl-1,3-propane, 1.000 g (3.31 mmol) 3.967 g calcium tungstate, 0.992 g zirconium oxide, 0.010 g Aerosil A 200 and 0.005 g iron (III) oxide were homogeneously mixed.

Immediately prior use 1.098 g Prepolymer-Paste and 1.000 g Diacrylamide-Paste were mixed homogeneously and polymerised at 37° C. for 8 hour. The radio-opacity according ISO 6876 is 12.7 mm/mm Al.

The invention claimed is:

1. A dental root canal sealing composition, which comprises (i) an amino terminated prepolymer having a viscosity at 23° C. of less than 100 Pas, which is obtained by reacting (a) one mole of a compound of the following formula (I)

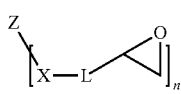

wherein
Z represents
an n-valent $C_{2-42}$ hydrocarbon group, which groups may contain 1 to 6 oxygen atoms, and which may be substituted by 1 to 6 $C_{1-4}$ alkyl groups;
X represents
a single bond or
an oxygen atom or a nitrogen atom substituted by a $C_{1-4}$ alkyl group;
L represents
a single bond or
an optionally substituted $C_{1-6}$ alkylene group, an optionally substituted $C_{6-14}$ arylene group, an optionally substituted $C_{7-16}$ alkylenearylene group, an optionally substituted $C_{7-16}$ arylenealkylene group,
which groups may be substituted by 1 to 6 $C_{1-4}$ alkyl groups; and
n represents
an integer of from 2 to 6; and
(b) at least n moles of one or more compounds
(b1) of the following formula (II)

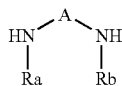

wherein
A represents a divalent saturated aliphatic $C_{2-16}$ hydrocarbon group or a divalent saturated cycloaliphatic $C_{3-6}$ hydrocarbon group, which groups may contain 1 to 6 oxygen atoms, and which may be substituted by 1 to 6 $C_{1-4}$ alkyl groups;
$R_a$ and $R_b$ are the same or different and represent a hydrogen atom, a $C_{1-6}$ alkyl or a $C_{3-14}$ cycloalkyl group, which may be substituted by one or more members of the group selected from a $C_{1-4}$ alkyl group, $C_{1-4}$ alkoxy group, a phenyl group, and a hydroxy group; or
(b2) of formula (III)

 R'NH$_2$ (III)

wherein R' represents
a substituted or unsubstituted $C_1$ to $C_{18}$ alkyl group,
a substituted or unsubstituted $C_3$ to $C_{18}$ cycloalkyl group,
a substituted or unsubstituted $C_7$ to $C_{30}$ aralkyl group, which groups may be substituted by one or more members of the group selected from a $C_{1-4}$ alkyl group, $C_{1-4}$ alkoxy group, a phenyl group, and a hydroxy group,
optionally in combination with a further di- or polyamine compound;
(ii) a compound capable of undergoing polyaddition with the aminoterminated prepolymer (i);

(iii) 40 to 85 wt.-% of a filler for providing a minimum radioopacity of at least 3 mm/mm Al.

2. The dental root canal sealing composition according to claim 1, wherein z represents a saturated aliphatic $C_{2-18}$ hydrocarbon chain which may contain 2 to 4 oxygen atoms, and which may be substituted by 1 to 6 $C_{1-4}$ alkyl groups or a substituted or unsubstituted $C_7$ to $C_{30}$ arylenealkylenearylene group which may be substituted by 1 to 6 $C_{1-4}$ alkyl groups.

3. The dental root canal sealing composition according to claim 1 or 2, wherein X is an oxygen atom and/or L is an alkylene group, preferably a methylene group, and/or wherein X-L is —OCH$_2$—.

4. The dental root canal sealing composition according to any one of the preceding claims, wherein n is 2.

5. The dental root canal sealing composition according to any one of the preceding claims, wherein the aminoterminated prepolymer is a prepolymer of one of the following formulas

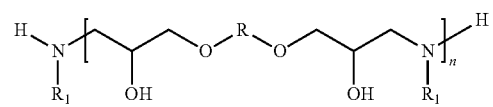

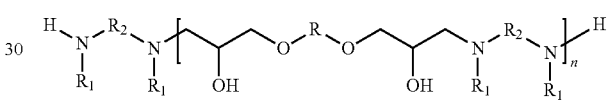

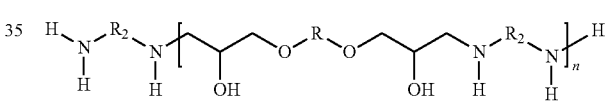

wherein
R represents a divalent substituted or unsubstituted $C_1$ to $C_{18}$ alkylene group, substituted or unsubstituted $C_{6-14}$ arylene group, substituted or unsubstituted $C_3$ to $C_{18}$ cycloalkylene group, substituted or unsubstituted $C_7$ to $C_{30}$ arylenealkylenearylene group,
$R_1$ represents
hydrogen or
a substituted or unsubstituted $C_1$ to $C_{18}$ alkyl group,
a substituted or unsubstituted $C_3$ to $C_{18}$ cycloalkyl group,
a substituted or unsubstituted $C_7$ to $C_{30}$ aralkyl group,
$R_2$ represents a divalent
substituted or unsubstituted $C_1$ to $C_{18}$ alkylene group,
a substituted or unsubstituted $C_3$ to $C_{18}$ cycloalkylene group,
a substituted or unsubstituted $C_7$ to $C_{30}$ aralkylene group, and
n is an integer.

6. The dental root canal sealing composition according to claim 5, wherein the aminoterminated prepolymer is a prepolymer of one of the following formulas

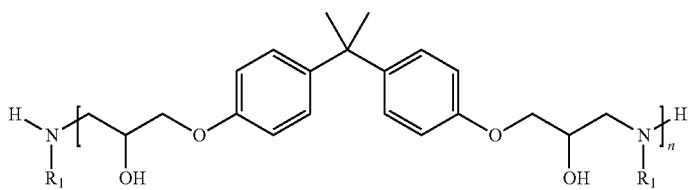

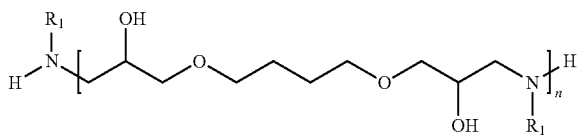

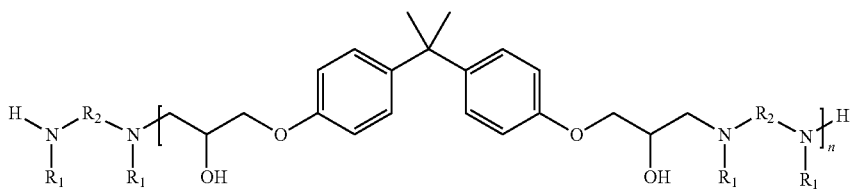

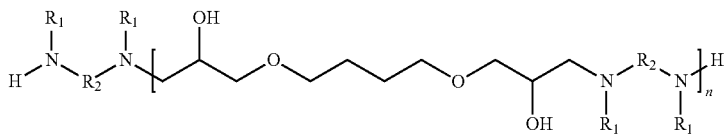

wherein $R^1$ and $R^2$ are defined as in claim 5.

7. The dental root canal sealing composition according to claim 1, wherein the compound capable of undergoing polyaddition with the aminoterminated prepolymer (i) is selected from a di- or polyfunctional acrylate, a di- or polyfunctional epoxide, a di- or polyfunctional isocyanate, a di- or polyfunctional isothiocyanate, a di- or polyfunctional acylamide, or a di- or polyfunctional maleimide.

8. The dental root canal sealing composition according to claim 1, wherein the filler contains $La_2O_3$, $ZrO_2$, $BiPO_4$, $CaWO_4$, $BaWO_4$, $SrF_2$, $Bi_2O_3$.

9. The dental root canal sealing composition according to claim 1, which is in the form of a two-component composition.

10. An amino terminated prepolymer having a viscosity at 23° C. of less than 100 Pas, which is obtained by reacting
(a) one mole of a compound of the following formula (I)

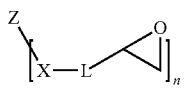

(I)

wherein
Z represents an n-valent $C_{2-42}$ hydrocarbon group, which groups may contain 1 to 6 oxygen atoms, and which may be substituted by 1 to 6 $C_{1-4}$ alkyl groups;
X represents
a single bond or
an oxygen atom or a nitrogen atom substituted by a $C_{1-6}$ alkyl group;

L represents
a single bond or
an optionally substituted $C_{1-16}$ alkylene group,
an optionally substituted $C_{6-14}$ arylene group,
an optionally substituted $C_{7-16}$ alkylarylene group,
an optionally substituted $C_{7-16}$ arylalkylene group,
which groups may be substituted by 1 to 6 $C_{1-4}$ alkyl groups; and
n represents an integer of from 2 to 6; and
(b) at least n moles of one or more compounds
(b1) of the following formula (II)

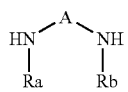

(II)

wherein
A represents a divalent saturated aliphatic $C_{2-16}$ hydrocarbon group or a divalent saturated cycloaliphatic $C_{3-6}$ hydrocarbon group, which groups may contain 1 to 6 oxygen atoms, and which may be substituted by 1 to 6 $C_{1-4}$ alkyl groups;
$R_a$ and $R_b$ are the same or different and represent a hydrogen atom, a $C_{1-6}$alkyl or a $C_{3-14}$ cycloalkyl group, which may be substituted by one or more members of the group selected from a $C_{1-4}$ alkyl group, $C_{1-4}$ alkoxy group, a phenyl group, and a hydroxy group;

or (b2) of formula (III)

$$R'NH_2 \quad (III)$$

wherein R' represents
- a substituted or unsubstituted $C_1$ to $C_{18}$ alkyl group,
- a substituted or unsubstituted $C_3$ to $C_{18}$ cycloalkyl group,
- a substituted or unsubstituted $C_7$ to $C_{30}$ aralkyl group, which groups may be substituted by one or more members of the group selected from a $C_{1-4}$ alkyl group, $C_{1-4}$ alkoxy group, a phenyl group, and a hydroxy group, optionally in combination with a further di- or polyamine compound, in a dental composition.

11. A process comprising manufacturing prefabricated root canal cones comprising the dental material of claim 1.

12. The dental root canal sealing composition according to claim 10, wherein the two-component composition is a powder/liquid or a paste/paste system.

* * * * *